United States Patent [19]
Lindqvist

[11] Patent Number: 6,045,855
[45] Date of Patent: Apr. 4, 2000

[54] ELECTROSTATIC COATING OF SMALL FALLING OBJECTS

[75] Inventor: Anders Lindqvist, Golvlaggaregatan 5, S-412 62 Göteborg, Sweden

[73] Assignees: Anders Lindqvist; Nils Lewinsky; Hasse Johansson, all of Göteborg, Sweden; a part interest of each

[21] Appl. No.: 09/125,398

[22] PCT Filed: Feb. 17, 1997

[86] PCT No.: PCT/SE97/00251

§ 371 Date: Aug. 18, 1998

§ 102(e) Date: Aug. 18, 1998

[87] PCT Pub. No.: WO97/29848

PCT Pub. Date: Aug. 21, 1997

[30] Foreign Application Priority Data

Feb. 19, 1996 [SE] Sweden ................................. 9600594

[51] Int. Cl.$^7$ ................................ B05D 1/06; B05B 5/025
[52] U.S. Cl. .................. 427/2.14; 427/475; 427/477; 427/478; 427/479; 427/483; 427/485; 427/213.31; 118/629; 118/636; 118/638
[58] Field of Search .................. 427/2.14, 2.18, 427/471, 475, 477, 483, 485, 213.31, 479, 478; 118/629, 638, 636

[56] References Cited

U.S. PATENT DOCUMENTS 2,270,341   1/1942   Ransburg .
4,510,170   4/1985   Cosentino et al. .
4,774,102   9/1988   Kiefer et al. .
5,470,603   11/1995  Staniforth et al. .
5,520,754   5/1996   Yaney et al. .

FOREIGN PATENT DOCUMENTS 0085149   4/1986   European Pat. Off. .
2 177 585  1/1987   United Kingdom .
WO92/14451 9/1992   WIPO .

*Primary Examiner*—Fred J. Parker
*Attorney, Agent, or Firm*—Burns, Doane, Swecker & Mathis, L.L.P.

[57] ABSTRACT

This invention relates to a process and a device for producing an even and homogenous coating of liquids or powders on small free-falling objects that are not earthed. The process and the device according to the invention are primarily intended for surface coating of medicinal products and foodstuffs. According to the invention, the non-earthed objects are positively or negatively charged in a suitable manner or not at all and are then caused to fall freely and individually through a substantially cylindrically-shaped zone (2), mainly along its central axis, where the coating substance, having first, in a suitable manner, been charged with a charge of opposite polarity to that of the objects or if these are not charged, with a positive or negative charge, is sprayed onto the particles by means of at least one or preferably at least two spray nozzles (3) which are placed peripherally around the zone (2) and directed mainly towards the central axis thereof, whereby the coating substance is attracted to the object because of the potential difference between them, and an even, homogenous surface coating is obtained.

20 Claims, 1 Drawing Sheet

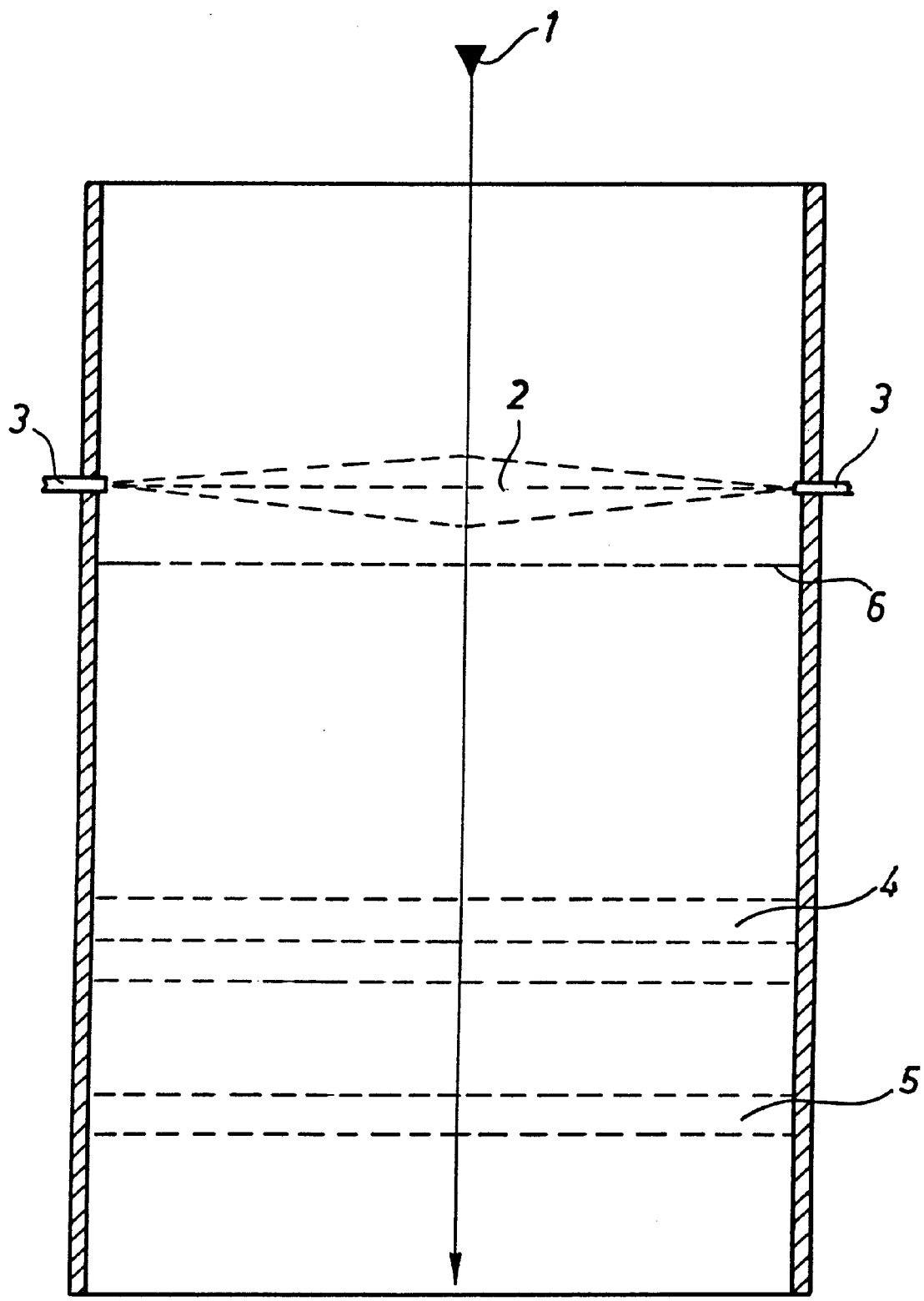

ELECTROSTATIC COATING OF SMALL FALLING OBJECTS

BACKGROUND AND SUMMARY

The present invention relates to a process and a device for electrostatic surface coating of small objects that are not earthed. More particularly, the invention relates to a process for forming an even and homogeneous coating of liquids or powder on small, free falling objects. The process and the device according to the present invention are mainly intended for coating of medicinal products and for surface coating of foodstuffs.

Surface coating of medicinal products in tablet form, is made for both medical, practical and aestethical reasons. Coating is made for example to facilitate administration, to hide unpleasant taste or smell, to improve mechanical properties of the medicine, to protect the active agents of the medicine from being destroyed by e.g. saliva or gastric juices or to protect the tablet in storage. Coating can also be used to bring about a controlled release of the medicine in the human body.

The processes which are used at present for coating of medicinal products involve rotating a large number of tablets in a slanting drum, known as a coating pan, or in horizontally mounted perforated cylinders, while at the same time the surface coating material, dissolved in a suitable substance, is poured or sprayed into the pan. The rotation of the tablets causes a tablet to move upwards in the coating pan along the side of the pan and then fall downwards in the middle of the pan on top of the bed formed by the tablets that are moving upwards. As the solvent of the coating material evaporates, the material will be deposited on the tablets.

A large problem with the current technology is that the tablets preferably should be spherical or at least be made by convex-shaped rounded dies. The reason therefor is that the existence of edges on the tablets may cause the coating applied thereon not to be even and homogeneous. However, tablets produced today usually have a flat, circular form, that is, they have a special edge surface to avoid problems with for instance caping of the tablet or increasing demands on the tablet-producing machine (deep concave dies, etc). The coating processes used today are batchwise and each batch goes through a large number of steps involving a large amount of manual work as well. The energy consumption is relatively high and the noise level is considerable. Space requirements are large, ventilation demands are stringent. These processes are time consuming as well.

Coating of confectionary, for example, the chocolate sweets known as "NON-STOP", is often performed in a similar manner.

In recent times, so called high speed methods for medicinal product coating have been developed, but in spite of this, the time needed to get finished dragées is about one to two working days. The cost of the substances the tablets are coated with often is fairly low, accounting for only a small amount of the total cost of the coating.

It is likewise known to perform the coating in a fluidizing bed. The tablets are made to move upwards through the bed propelled by a gas, preferably air, while the coating is being sprayed on.

Processes for electrostatic coating of small objects have been known for some time. A feature often common in earlier known technologies is that the objects to be coated are earthed, see for example U.S. Pat. No. 4,774,102, wherein a process for electrostatic spray coating of a not earthed object is described.

Electrostatic coating of medicinal products is also previously known; for example in WO 92/14451, such a process is described. According to the process of that publication, medicinal products are coated with a dry powder by using a procedure according to which the medicinal products are placed on a transportation device on which they are coated with a powder. The potential difference between the medicinal product and the powder or between the transportation device and the powder is used to attract the powder to the medicinal products. In this way those parts of the medicinal products that are in contact with the transportation device receive no coating. The powder coating is finally treated, for example by heating, to make a fused film on the medicinal product. The other side of the medicinal product can then be coated in the same way.

A big disadvantage with this earlier known technology, particularly in surface coating of tablets, is that in almost all cases the earthing is achieved by placing the objects on some kind of support, for example a conveyor. This means that the objects are being coated on one side at a time and that there is a considerable risk that an edge will form in the border zone between the surface coatings of the two sides. This in turn means that the coating will not be even and homogeneous, a feature that is especially important in the coating of medicinal products to bring about a slow, controlled release of a medicine into the human body.

EP-B-0 085 149 describes a process and a device for electrostatic coating of an object that is not earthed, with a liquid or a powder. According to this process, the objects to be surface coated are made to fall, by means of a stationary dispersal (spreader) system, as a continous circular curtain along the walls of a non-conductive tube, where the objects are passed through a corona zone and receive a positive charge. Centrally in this tube a centrifugal spreading device is placed. In the device, the material in liquid or particle form to be applied on the objects is negatively charged by passage through a negative corona zone and by means of this device the material is then sprayed on to the continuous curtain that the objects form. The process seems mainly intended for addition of substances such as vitamins, antibiotics and amines to different powders and pellets or for the moisturizing of granulates and masses in powder form but not for surface coating of the type necessary for coating of medicines.

In the descriptive part of the above patent, many examples of application areas for the invention are given, but they all concern addition of some substance to materials such as skimmed milk, fertilizers, fungicides and the like. If the process were to be used for surface coating there would be several serious disadvantages. Among them a large risk that the objects in the continuous curtain collide with each other or with the walls of the tube, resulting in a newly applied surface coating being subjected to mechanical stresses, which can cause damage to the coating. It is also difficult to produce a completely even and homogeneous coating since the objects receive spray from one direction only. Additionally, there is no mention in the above patent that the process could be used for producing a hard surface, which is necessary in the coating of medicinal products.

Electrostatic surface coating in accordance with the present invention is carried out in one or a few steps and can be automated. The surface coating can be effected continuously and at the pace of production of the product. Furthermore, it is not necessary to electrically charge the objects. It is sufficient to charge the substance the objects are to be coated with, something that is especially favourable in the coating of medicinal products, as such products may be damaged by a possible charge.

The process of using electrostatic surface coating of small free-falling, not earthed objects with a substance in powder or liquid form, according to this invention is characterized in that the objects are charged positively or negatively in a suitable manner. This first step can also be omitted because uncharged objects can also be coated by using the concept of the present invention. After a possible charge, the objects are made to fall freely and individually through a mainly cylindrically shaped zone, essentially along the central axis of the zone, where the substance in powder or liquid form, having first received, in a suitable manner, a charge of the opposite sign to that of the objects, or if these are not charged, with an optional charge, is sprayed onto the particles by means of at least one spray nozzle, preferably at least two spray nozzles, placed peripherally around the zone and directed essentially towards the central axis thereof, whereby the substance in powder or liquid form is attracted to the objects because of the potential difference between the objects and the substance and an even and homogeneous surface coating is obtained.

The invention also refers to a device for electrostatic surface coating of small free-falling objects which are not earthed, with a substance in powder or liquid form, characterized in that it comprises at least an essentially cylindrical zone, a means for the supply of positively charged, negatively charged or uncharged objects to a central part passing through the essentially cylindrically shaped zone, and means for spraying a positively or negatively charged substance in powder or liquid form towards the central part passing through the cylindrically shaped zone.

BRIEF DESCRIPTION OF THE DRAWINGS

The invention will be described in more detail in the following by way of a preferred not limiting embodiment and with reference to the attached skeleton drawing.

DETAILED DESCRIPTION

The objects (1), preferably tablets, to be coated with a surface layer of a substance in powder or liquid form, are charged positively or negatively in a suitable prior-art manner, for instance by passage through a corona zone (not shown in the drawing). This first step can also be omitted. After that, the charged or uncharged objects are made to fall freely and essentially individually, preferably centrally through a cylindrically shaped zone (2). In this zone the objects are sprayed with the substance in powder or liquid form, said substance in turn having first been charged positively or negatively in any known manner, by means of one or preferably two, peripherally placed spray nozzles 3. If only one nozzle is used, it is preferably annular and is placed around essentially the whole zone (2). The nozzles 3 are placed so as to be directed mainly towards the vertical axis of the zone (2). A governing and regulating device (not shown in the drawing) and a suitable dosing apparatus (not shown in the drawing) ensure that the electrically charged powder or liquid substance that is sprayed into the zone (2) always has the correct volume, quantity and position. The powder or liquid substance will, because of the potential difference from that of the freely falling objects, be attracted to the objects and form a homogeneous layer on the surface of the objects.

The surface coated objects then pass through a zone (4) where the applied substance will be made to form a hardened layer preferably by tempering, cooling, coagulation, drying or the like.

Optionally, the surface-coated objects are then passed through an electrical field (5) for the neutralizing of remaining electrical charges before the surface-coated objects come into contact with an earthed surface. The purpose of this step is to prevent sparking, as might otherwise form as the surface-coated objects, still possessing some residual charge, come into contact with an earthed surface.

The thickness of the surface coating of the powder or liquid substance is regulated by means of the magnitude of the applied potential difference.

In accordance with a preferred embodiment, only the liquid or powder substance that is to form the surface coating is charged, either positively or negatively, while the objects to be coated are uncharged.

A barrier zone (6) can be arranged under the zone (2) to prevent any superfluous surface coating material from falling down together with already coated objects.

The device according to the invention can be coupled directly to the equipment used for the production of the tablets and coat the tablets as they are being produced. This means that a very large part of today's cost for work and premises can be saved. This so called direct coating system also reduces dust formation and minimizes the risks of handling damages to the tablets. With the process and equipment according to this invention the noise level is also much reduced.

This invention is primarily intended to be used for coating of tablets, but is is also equally useful for surface coating of capsules, suppositories, granulates and for surface coating of confectionary and other kinds of foodstuffs. In these instances the surface coating can be of very different kinds, such as sugar, cacao powder, calcium carbonate, polyethylene glycoles, cellulose derivatives or polyacrylates.

The invention can also be used within completely different areas for instance for surface coating of electronic components or for producing rust protection in the mechanical industry.

The invention is not limited to the above mentioned examples, but can be modified in several different ways within the scope of the attached patent claims.

What is claimed is:

1. A process for electrostatic surface coating of non-earthed free-falling objects with a coating substance, comprising the steps of:
   causing objects to fall freely and individually through a substantially cylindrically shaped spraying zone substantially along a central axis of the spraying zone;
   giving a coating substance an electrical charge that is different from a charge of the objects;
   spraying the charged coating substance on the objects with at least one spray nozzle placed peripherally around the spraying zone and directed substantially towards the central axis thereof such that the coating substance is attracted to the objects because of a potential difference between the coating substance and the objects and an even and homogenous coating is obtained on the objects.

2. The process according to claim 1, comprising the further step of causing the objects to pass through a hardening zone in which the coating is hardened after the objects are caused to pass through the spraying zone.

3. The process according to claim 1, comprising the further step of causing the objects to pass through an electrically neutralizing zone in which remaining charges on the objects and the coating are neutralized.

4. The process according to claim 1, wherein the at least one spray nozzle is a substantially annular nozzle placed around the spraying zone.

5. The process according to claim 1, comprising a further step of adjusting a thickness of the coating by adjusting a potential difference between the objects and the coating substance.

6. The process according to claim 1, wherein the objects are medicinal products.

7. The process according to claim 1, wherein the objects are foodstuffs.

8. The process according to claim 2, comprising the further step of causing the objects to pass through an electrically neutralizing zone in which remaining charges on the objects and the coating are neutralized.

9. The process according to claim 2, wherein the at least one spray nozzle is a substantially annular nozzle placed around the spraying zone.

10. The process according to claim 3, wherein the at least one spray nozzle is a substantially annular nozzle placed around the spraying zone.

11. The process according to claim 8, wherein the at least one spray nozzle is a substantially annular nozzle placed around the spraying zone.

12. The process according to claim 1, comprising a further step of adjusting a thickness of the coating by adjusting a potential difference between the objects and the coating substance.

13. The process according to claim 3, comprising a further step of adjusting a thickness of the coating by adjusting a potential difference between the objects and the coating substance.

14. The process according to claim 4, comprising a further step of adjusting a thickness of the coating by adjusting a potential difference between the objects and the coating substance.

15. The process according to claim 8, comprising a further step of adjusting a thickness of the coating by adjusting a potential difference between the objects and the coating substance.

16. A device for electrostatic surface coating of non-earthed objects, comprising:

a substantially cylindrically shaped spraying zone;

a device for delivery of objects to a central part of the spraying zone such that the objects are caused to fall freely and individually through the spraying zone and along a central axis of the spraying zone; and a device for spraying a coating substance having an electrical charge different from an electrical charge of the objects in a direction towards the central part of the spraying zone.

17. A device according to claim 16, further comprising a hardening zone downstream of the spraying for hardening a coating applied on the objects.

18. The device according to claim 16, further comprising a neutralizing zone downstream of the spraying zone and including means for neutralizing charges remaining on coated objects after the coating substance.

19. The device according to claim 16, wherein the spraying device includes means for collection of superfluous coating substance.

20. The device according to claim 17, further comprising a neutralizing zone downstream of the spraying zone and including means for neutralizing charges remaining on coated objects after the coating substance.

* * * * *